United States Patent
Bacon et al.

(10) Patent No.: US 8,753,647 B2
(45) Date of Patent: Jun. 17, 2014

(54) LIPOSOMAL VACCINE COMPOSITIONS COMPRISING A POLYSACCHARIDE ANTIGEN AND A PROTEIN ADJUVANT

(75) Inventors: Andrew David Bacon, London (GB); Gregory Gregoriadis, London (GB); Peter Laing, London (GB)

(73) Assignee: Lipoxen Technologies Limited, London (GB)

( * ) Notice: Subject to any disclaimer, the term of this patent is extended or adjusted under 35 U.S.C. 154(b) by 1069 days.

(21) Appl. No.: 12/088,672

(22) PCT Filed: Sep. 29, 2006

(86) PCT No.: PCT/EP2006/066935
§ 371 (c)(1),
(2), (4) Date: Aug. 19, 2008

(87) PCT Pub. No.: WO2007/039583
PCT Pub. Date: Apr. 12, 2007

(65) Prior Publication Data
US 2008/0317838 A1  Dec. 25, 2008

(30) Foreign Application Priority Data
Sep. 30, 2005  (EP) .................................... 05256160

(51) Int. Cl.
*A61K 39/116* (2006.01)
(52) U.S. Cl.
USPC .................... 424/203.1; 424/236.1; 424/282.1
(58) Field of Classification Search
None
See application file for complete search history.

(56) References Cited

U.S. PATENT DOCUMENTS 4,686,102 A * 8/1987 Ritchey et al. ............. 424/244.1

FOREIGN PATENT DOCUMENTS

| WO | WO-91/01143 | 2/1991 |
|---|---|---|
| WO | WO-92/02243 | 2/1992 |
| WO | WO-92/20370 | 11/1992 |
| WO | WO-99/03501 | 1/1999 |
| WO | WO-99/22763 | 5/1999 |
| WO | WO-99/65465 | 12/1999 |
| WO | WO-2004/041866 | 5/2004 |

OTHER PUBLICATIONS

Mirchamsy et al. (Biologicals, 24:343-350, 1996).*
Abraham et al., Journal of Immunology (1992) 149(11):3719-3726.
Burgeot et al., Vaccine (2001) 19:2092-2099.
International Search Report for PCT/EP2006/066935, mailed on Dec. 28, 2006, 4 pages.
Lett et al., Infection and Immunity (1995) 63(7):2645-2651.
Pietrobon et al., Immunomethods (1994) 4:236-243.
Pappenheimer et al., Immunochem. (1972) 9:891-906.
Uchida et al., J. Biol. Chem. (1973) 248:3838-3844.
Uchida et al., J. Biol. Chem. (1973) 248:3845-3850.

* cited by examiner

*Primary Examiner* — Brian J Gangle
(74) *Attorney, Agent, or Firm* — One3 IP Management, PC; Dean G. Stathakis; Peter D. Weinstein

(57) ABSTRACT

A liposomal composition, preferably a vaccine, comprising liposomes formed of liposome forming compounds, containing coentrapped polysaccharide antigen and T-cell dependent protein carrier, such as tetanus toxoid or diphtheria toxin modified to render it non-toxic. The invention is of use in the production of vaccines against *Haemophilus influenzae*, *Streptococcus pneumoniae* or *Neisseria meningitidis*.

33 Claims, 2 Drawing Sheets

Figure 1:
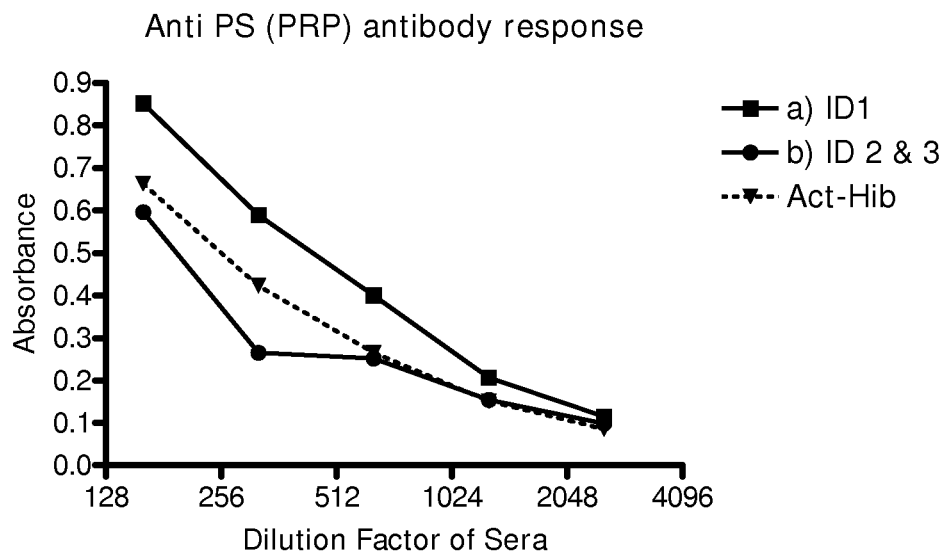

LIPOSOMAL VACCINE COMPOSITIONS COMPRISING A POLYSACCHARIDE ANTIGEN AND A PROTEIN ADJUVANT

CROSS-REFERENCE TO RELATED APPLICATIONS

This application is the national phase of PCT application PCT/EP2006/066935 having an international filing date of 29 Sep. 2006, which claims benefit of European Application No. 05256160.2 filed 30 Sep. 2005. The contents of the above patent applications are incorporated by reference herein in their entirety.

The present invention relates to liposomal compositions, in particular compositions useful for eliciting an immune response against polysaccharide antigens, in particular derived from pathogenic microbes, such as pneumococcal and Hib polysaccharide antigens.

Bacterial infections caused by encapsulated bacteria are a major world health problem. The species *Streptococcus pneumoniae*, *Haemophilus influenzae* and *Neisseria meningitidis* are difficult to vaccinate against due to the thymus independent nature of the major surface antigens, the capsular polysaccharides.

T-cell independent antigens present particular problems regarding the development of effective vaccines. Antibody production is low and is not normally boosted by re-immunisation. The antibody isotypes are restricted to IgM and other isotypes are generally of low affinity for a specific antigen.

A major problem lies in the response of young children to T-cell independent vaccines. These individuals are amongst the most vulnerable such bacterial infections. This age group responds most poorly to T-cell independent antigens.

Various methods have been attempted to adjuvantate polysaccharide antigens. For instance polysaccharides have been conjugated to carrier proteins such as tetanus toxoid, which results in some improvement in immunogenic effect. The polysaccharides have alternatively been formulated with liposomes, which also gives an enhanced immune response.

Burgeot, C. et al in Vaccine 2001, 19, 2092-2099, disclose immunopotentiation of polysaccharide vaccine from *Staphylococcus aureus* co-entrapped in liposomes with alpha toxin. The liposomes were formed of liposome forming compounds containing egg phosphatidylcholine, stearylamine and cholesterol in molar ratios of 7:2:1. The liposomes were formed using the dehydration rehydration method, with dehydration of a mixture of empty SUV and antigens suspended in a 10 mM Hepes (pH 7.4), 150 mM sodium chloride buffer. The ratio of polysaccharides to toxin protein ranged from 20 to 5. Alpha toxin is a highly toxic substance and is haemolytic. The authors reason that its activity in potentiating the antigenicity of the polysaccharide antigen is dependent upon the properties it exhibits as a toxin involving puncturing of the cell membrane. They show that the potentiation is not achieved with heat inactivated toxin derivative. Alpha toxin has a subunit molecular weight of about 33 kDa.

Pietrobon, P. J. F. et al in Immunomethods 4, 236-243 (1994) describe co-entrapment into liposomes of the T independent antigen LPS (which is not water-soluble) and a polypeptide with T-cell recognition sites, haemagglutinin (HA). The liposome sizes are not disclosed. The weight ratio of LPS to HA is in the range 2:1 to 1:10. The liposomes are made by forming a lipid film containing LPS and HA and hydrating this in aqueous suspending liquid containing n-octylglucopyranoside. HA is not inert, but binds to various cell surface receptors via sialic acid bearing glycons and stimulates an innate immune response. Compounds which stimulate an innate immune response may generate undesirable inflammation.

According to the invention there is provided a new liposomal composition comprising coentrapped within liposomes a polysaccharide antigen and a protein carrier; wherein the polysaccharide antigen is water-soluble and the protein carrier has at least one T-cell epitope, a molecular weight of at least 35 kDa, and is non-toxic; wherein the polysaccharide antigen and protein carrier are non-conjugated; and the liposomes have an average diameter in the range 50-700 nm and are formed from liposome forming compounds having, in combination, no overall ionic charge and comprising at least one phospholipid.

In the invention, the term "coentrapped" means that the two actives, namely the polysaccharide antigen and the protein carrier, must be associated with the same liposome. Although association may be solely with the outer surface of liposomes, it is preferred that the actives are at least in part entrapped in the intravesicular space of the liposomes. Both actives should be water-soluble and thus located in the aqueous phase of the liposomal formulations. Where the liposomes are multilamellar the actives may be between lamellae.

In the invention it is important that the polysaccharide antigen and the protein carrier are not covalently conjugated to one another. This has the great advantage of allowing coformulation of many ingredients especially different antigens to form a multivalent antigen composition and avoiding the chemical conjugation step that would be necessary for such conjugation.

The protein carrier is non-toxic to a mammalian body and should not stimulate an innate immune response when administered thereto. Thus, the carrier is effectively 'inert' in the mammalian body. This is in contrast to protein adjuvants which are not biologically inert but engage (either directly themselves, or via components that they release from killed host cells) host receptors to elicit cellular responses from the cells of the immune system in the form of an innate immune response.

The carrier protein has a molecular weight high enough for it to act as a T-cell dependent antigen. The molecular weight is at least 35 kDa, for instance up to 1000 kDa, eg in the range 75-400 kDa. The present invention can use proteins which have been used as carriers for T-cell independent antigens in the prior art, such as ovalbumin, tetanus toxoid and diphtheria toxoid. The protein should generally be non-haemolytic, and non-toxic. In terms of non-toxicity, for instance, the protein should have an LD50 in excess of 4 mg/kg (in mice, iv or sc). Preferably the protein should be level 6 on the Hodge & Sterner scale, ie be Relatively Harmless.

Suitable proteins include ovalbumin, tetanus toxoid, diphtheria toxoid and diphtheria CRM197 (a genetic mutant of diphtheria toxin). Tetanus toxoid has a molecular weight of about 100 kDa. Tetanus toxoid and diphtheria CRM 197 (a genetic mutant of the toxin) fail to elicit the significant immune response elicited by the corresponding toxins. This is thought to be due to attenuation by formaldehyde or genetic mutation. These carriers do, however, elicit an adaptive immune response by activation and the subsequent proliferation of T-helper cells that are needed for antibody responses.

Preferably, the liposomal composition is in unit dosage form and comprises 1-30 µg of the protein carrier, more preferably 10-30 µg. Such dosages are believed to be suitable for administration to a subject in need of immunisation, such as a human.

In the invention, the polysaccharide antigen is preferably derived from an infectious agent, preferably a pathogenic bacterium, for instance selected from *Haemophilus influenzae, Streptococcus pneumoniae, Neisseria meningitidis, E. coli*, or group B *Streptococcus*. Most preferably the antigen is derived from *Haemophilus influenzae* or *Streptococcus pneumoniae*. The polysaccharide antigen is preferably a T-cell independent antigen. In the composition of the invention, the weight ratio of polysaccharide antigen to protein carrier is preferably in the range 6:1 to 1:6, more preferably 4:1 to 1:3. Preferably, there is an excess of polysaccharide to protein in the composition.

In the invention, there may be single polysaccharide antigen but preferably the composition is multivalent, that is it comprises several polysaccharide antigens in admixture. The composition may comprise two or more, three or more, five or more, seven or more, for instance up to 40, preferably in the range 7 to 23 polysaccharide antigens. Preferably, the antigens are derived from the same bacterial species. The antigens in such a multivalent composition may be co-encapsulated in liposomes, or there may be several populations, the liposomes of which each contain a separate antigen or antigen mixture distinct from the other populations. Preferably the antigens are separately entrapped in liposomes, that there is a district population for each polysaccharide antigen. This allows optimum flexibility in terms of generating a variety of different thereof vaccines from common starting-materials.

The liposomes comprise compounds having no overall ionic charge. The compounds are preferably neutral, including zwitterionic compounds with one anionic and one cationic charge, but may contain small quantities of anionic or cationic compounds provided these are charge-balanced with oppositely charged compounds. Preferably the compounds comprise phosphatidylcholine compounds and/or phosphatidylethanolamine compounds. The liposome-forming compounds are usually amphiphilic, i.e. consist of a hydrophobic component and a hydrophilic component. The hydrophobic components are generally provided by acyl chains but the liposome-forming compounds may alternatively be glycerol-ether based lipid compounds. Non lipidic compounds, that is not based on glycerol compounds, may be included if desired, for instance non-ionic surfactant type materials. Preferably the compositions comprise cholesterol, for instance in a molar amount of at least 10%, preferably at least 25%, based on total liposome forming components.

The composition of the invention may be in the form of an aqueous suspension, that is in which the liposomes are suspended in a continuous aqueous medium. Alternatively the composition may be a precursor of such an aqueous composition, which may be diluted with water or an aqueous liquid to form the aqueous suspension. Such precursors may be in the form of dried materials, especially in powder form, for instance provided by spray drying or freeze drying (lyophilisation).

The compositions of the invention may further comprise (a) diluent(s) and/or excipient(s). Since the compositions are intended to be used directly or after intermediate formulation steps, e.g. dilution, to be administered to mammalian subjects, the diluents or the excipients are preferably pharmaceutically acceptable. Suitable excipients are known.

It is particularly preferred that the composition comprises sugars. Sugars may assist stabilisation of the liposomes during formation of the liposomes and/or in storage. Preferably the liposomes are formed by the dehydration-rehydration method, empty small unilamellar vesicles (SUV's) (e.g. made by hydration of dry lipid film to form multi-lamellar vesicles (MLV) and sonication to SUV) and active (polysaccharide antigen and protein carrier) are suspended in an aqueous liquid prior to drying preferably by lyophilisation. The dried product is then rehydrated and optionally subjected to steps to remove non-entrapped material, over-sized liposomes or to reduce the average liposome size, by methods known to the person skilled in the art.

For improved control of rehydrated vesicle size, the method used includes sugar in the suspending liquid of the dehydration step, as discussed in WO99/65465. The sugar may be selected from monosaccharides such as glucose and fructose, disaccharides such as lactose and sucrose as well as polysaccharides. A particularly preferred sugar is a di-saccharide such as trehalose, sucrose or lactose or a monosaccharide such as glucose. In particular the preferred sugar is sucrose.

In such methods, the amount of sugar is such that mass ratio of sugar to liposome forming compound is in the range of from 1:1 to 6:1 w/w, most preferably from 1:1 to 5:1. With higher levels of sugar, the encapsulation efficiency of the method is reduced. With lower amounts of sugar, however, the control over the size of the final liposomes is lost.

The invention further provides a process for process for producing the new composition in which the polysaccharide antigen and protein carrier are co-encapsulated in liposomes.

Preferably the methods described above are used for the encapsulation. Sugar need not be used but preferably is used in these dehydration-rehydration methods. The empty liposomes are preferably small or medium sized and may be multilamellar or unilamellar.

The product liposomes have average diameter in the range 50 to 700 nm, preferably in the range 80 to 500 nm, more preferably in the range 80 to 300 nm. Preferably the composition contains very low levels of liposomes with diameters greater than 1500 nm, even more preferably very low levels of liposomes with diameters greater than 1000 nm. The level of very small liposomes, e.g. less than 20 nm should also be kept as low as possible. The sizes are measured by photon correlation spectroscopy.

The invention also provides the use of the liposomes and compositions in the manufacture of a medicament for administration to a mammal to elicit an immune response to the polysaccharide antigen.

Preferably the immune response involves production of IgG at least, to the polysaccharide antigen, and additionally preferably IgM and IgA, preferably so that a protective effect to a challenge from the infectious micro organism is achieved in the recipient.

Preferably the composition is administered subcutaneously, intravenously, intraperitoneally, intramuscularly, intranasally, by inhalation, intravaginally, buccally or orally. Most preferably the composition is administered subcutaneously.

Generally the administration is for protective purposes to provide a response against infection by an infectious microbe, especially an infectious bacterium, of the type mentioned above. The subject to which the composition is administered may be a mammal of any age, in need of having protective immunity. The invention is of most value for treating humans. For instance administration may be to provide resistance to seasonal outbreaks, specific outbreaks of the infections, or may be part of health programmes especially for infants. The invention is of particular value for the treatment of human infants having reduced immune responses to T-cell independent antigens, for instance polysaccharide antigens, for instance being less than two years of age.

The invention further provides methods of administering the compositions.

Further preferred embodiments of the invention are mentioned in the claims.

Figure 2:
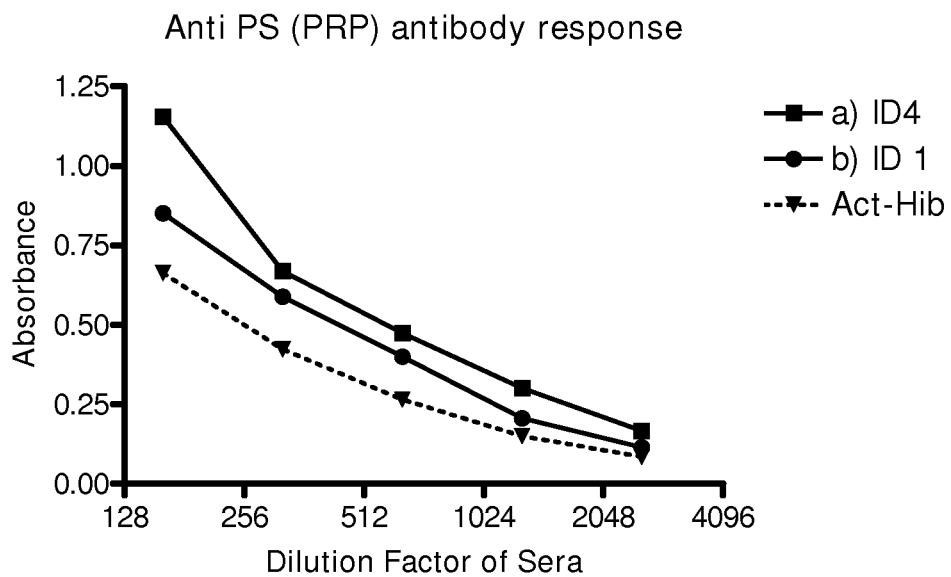
Figure 3:
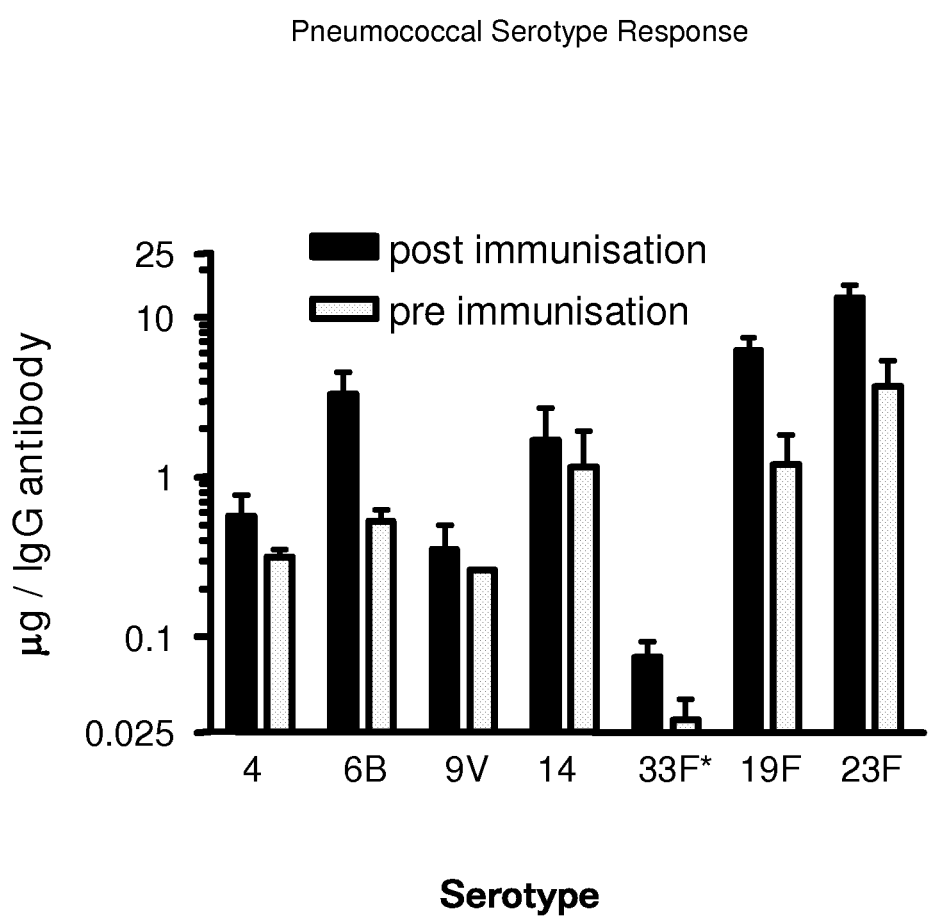

The following examples illustrate the invention and refer to the following figures, in which FIG. 1 shows the Anti PS (PRP) antibody response of mice when administered formulations ID1, ID2 & 3 and ACT-HIB® without cholesterol (Example 1);

FIG. 2 shows the Anti PS (PRP) antibody response of mice when administered formulations ID4, ID1, and ACT-HIB® with cholesterol (Example 1); and FIG. 3 shows the IgG antibody response pre and post immunisation to seven serotypes tested (Example 2).

EXAMPLE 1

Demonstration of anti polysaccharide response, in mice, to liposomal polysaccharide vaccines in compared to a licensed (in man) polysaccharide vaccine delivery of polysaccharide.

Experimental Details:—

The following liposome formulations (ID1-6) were prepared, Table 1, using a conventional lipid film dry/hydration to MLV/sonication to small unilamellar vesicles (SUV)/DRV process (WO9965465). Sucrose ×3 lipid mass was added to the SUV and material(s) to be entrapped at the SUV stage prior to DRV process to reduce the size of the resultant liposomes formed post the DRV stage. The average diameter of the DRV by photon correlation spectroscopy is about 500 nm.

TABLE 1

Liposomal formulations prepared. (ID1-6)

| Lipid composition (molar ratio) | Materials entrapped ($^a$ = co-entrapped) | | |
|---|---|---|---|
| | Tetanus Toxoid and PS (Hib PRP)$^a$ | Tetanus Toxoid | PS (Hib PRP) |
| EPC:DOPE:DOTAP (4:2:1) | ID1 | ID2 | ID3 |
| Soya PC:Cholesterol (11:9) | ID4 | ND | ND |

Material details:—The lipidic materials Egg PC (EPC, 98% purity, Lipoid) and Hydrogenated Soya PC (SPC-3, 0.98% purity, Lipoid) were obtained form Lipoid GmbH. Whilst dioleoyloxyphosphatidylethanolamine (DOPE) (AVANTI® Product Number: 850725) were obtained from AVANTI® Polar Lipids and, 1,2-dioleoyloxy-3-trimethylammonium propane (DOTAP) was obtained form Merck Chemicals Ltd. Purified polyribose ribitol phosphate capsular polysaccharide (PRP-PS) of *Haemophilus influenzae* type b and Tetanus Toxoid material were obtained from the Serum Institute of India (SII). entrapment efficacies were tested for PS and protein for ID1 and 4. For both materials for ID1 the values were around 90%. For both materials for ID4 values were around 70%.

The EPC without cholesterol formulations in Table 1 were tested for their ability to induce a antibody response to the polysaccharide antigen in mice. Mice (CD-1), were dosed once subcutaneously with a) formulation ID1 or b) formulations ID2 and 3, mixed immediately prior to dosing. A licensed vaccine product for the induction of protective levels of anti PRP (PS) antibodies in humans ACT-HIB® (a vaccine of purified polyribose ribitol phosphate capsular polysaccharide (PRP) of *Haemophilus influenzae* type b, covalently bound to tetanus toxoid protein) was used as a comparator positive control. All doses were normalised with respect to the dose of PRP (PS) and TT administered, 2 and 4 μg respectively.

The results are shown in FIG. 1.

Comments

The results of the anti PS (PRP) antibodies generated following immunisation with a) ID1, b) ID2 & 3 and, ACT-HIB® clearly indicate that:— a) the co-delivered TT and PS (PRP) with the same liposomal vehicle (ID1) formulation produce a higher antibody response than the same materials TT and PS (PRP) dose but administered in separate liposomal vehicles (ID2 and 3 respectively); and b) the co-delivered TT and PS (PRP) with the same liposomal vehicle (ID1) formulation produce a higher antibody response than the same materials TT and PS (PRP) dose administered in the form of a protein polysaccharide conjugate vaccine (ACT-HIB®).

The Soya PC with Cholesterol formulations in Table 1 were tested for their ability to induce an antibody response to the polysaccharide antigen in mice. Mice (CD-1), were dosed once subcutaneously with a) formulation ID4 or b) formulation ID1, mixed immediately prior to dosing. A licensed vaccine product for the induction of protective levels of anti PRP (PS) antibodies in humans ACT-HIB® (a vaccine of purified polyribose ribitol phosphate capsular polysaccharide (PRP) of *Haemophilus influenzae* type b, covalently bound to tetanus (toxoid) protein) was used as a comparator positive control. All doses were normalised with respect to the dose of PRP (PS) and TT administered, 2 and 4 m respectively.

The results are shown in FIG. 2.

Comments

The results of the anti PS (PRP) antibodies generated following immunisation with a) ID4, b) ID1 and, ACT-HIB® clearly indicate that:— a) the co-delivered TT and PS (PRP) with the same liposomal vehicle (ID3) formulation (with Cholesterol) produce a higher antibody response than the same materials TT and PS (PRP) dose administered in the form of a protein polysaccharide conjugate vaccine (ACT-HIB®); and b) the co-delivered TT and PS (PRP) with the same liposomal vehicle (ID4) formulation (with Cholesterol) produce a higher antibody response than the same materials TT and PS (PRP) dose administered in a liposomal formulation (ID1) without cholesterol.

EXAMPLE 2

Demonstration of multivalent anti *Streptococcus pneumoniae* polysaccharide serum IgG responses, in mice, following immunisation of a blend (multivalent) of monoserotype liposomal compositions comprising of coentrapped pneumococcal polysaccharide and protein diphtheria toxin (197) CRM Mutant within liposomes.

Experimental Details:—

The following liposome formulations (ID7-20) were prepared, Table 2, using a conventional lipid film dry/hydration to MLV/sonication to SUV/DRV process (i.e. as in Example 1). Sucrose ×3 lipid mass (SUV) was added to the SUV and material(s) to be entrapped at the SUV stage prior to DRV process to reduce the size of the resultant liposomes formed post the DRV stage.

Each formulation (ID7-20), consisted of an individual pneumococcal polysaccharide serotype coentrapped with the protein diphtheria toxin CRM197 mutant within liposomes. The mutant form of diphtheria toxin is described and was isolated as Uchida, Jr., T., Pappenheimer, Jr., A. M., Greany, R., (1973) J. Biol. Chem. 248, 3838-3844. and Uchida, Jr., T., Pappenheimer, Jr., A. M., Harper, A. A., (1973) J. Biol. Chem. B 248, 3845-3850. CRM197 is a non-toxic DT mutant containing a lesion in the A chain blocking ADP-ribosylation. CRM results from a base change in the structural gene resulting in the substitution of glutamic acid for glycine. While CRM shows no enzymatic activity, it is immunologically identical to diphtheria toxin. (Pappenheimer, Jr., A. M., Uchida, T. and Harper, A. A. (1972) Immunochem. 9, 891-906.)

CRM197 is similar to diphtheria toxoid. CRM197 is a well defined protein in contrast to formaldehyde treated toxin (toxoid) which is non-specifically cross linked. On SDS gels, the CRM197 protein migrates as a single major band of approximate molecular weight 63,000 daltons

TABLE 2

Liposomal mono PS entrapped formulations prepared. (ID7-20)

| Formulation ID | Lipid (SUV), mg | Diphtheria Toxin CRM197, µg | Pneumococcal Polysaccharide | |
|---|---|---|---|---|
| | | | µg | (Serotype) |
| ID7 | 7.81 | 21 | 84 | 1 |
| ID8 | 7.81 | 21 | 84 | 2 |
| ID9 | 7.81 | 21 | 84 | 4 |
| ID10 | 7.81 | 21 | 84 | 5 |
| ID11 | 7.81 | 21 | 84 | 6B |
| ID12 | 7.81 | 21 | 84 | 7F |
| ID13 | 7.81 | 21 | 84 | 9N |
| ID14 | 7.81 | 21 | 84 | 9V |
| ID15 | 7.81 | 21 | 84 | 12F |
| ID16 | 7.81 | 21 | 84 | 14 |
| ID17 | 7.81 | 21 | 84 | 15B |
| ID18 | 7.81 | 21 | 84 | 19F |
| ID19 | 7.81 | 21 | 84 | 23F |
| ID20 | 7.81 | 21 | 84 | 33F |

Material details:—The lipidic materials used were Egg PC (E PC, 98% purity, Lipiod) and cholesterol (Sigma). Pneumococcal capsular polysaccharide (Pn PS) equivalent to the American Type Culture Collection (ATCC).materials and diphtheria toxin CRM197 protein were obtained from the Serum Institute of India Limited (SIIL).

The liposomal mono PS entrapped formulations (ID7-20) were individually rehydrated (DRV process) and pooled together to make a multivalent formulation immediately before immunization, via subcutaneous injection, of five CD1 mice (female). The dose of the multivalent vaccine contains the equivalent of 14 monovalent formulations containing 6 µg pneumococcal polysaccharide and 1.5 µg diphtheria toxin CRM197 protein and 0.559 mg of lipid. Consequently, the multivalent (14 serotypes) vaccine administered to the mice contain in total 84 µg pneumococcal polysaccharide and 21 µg diphtheria toxin CRM197 protein and 7.81 mg of lipid.

The mice received a total of two immunisation doses 21 days apart, additionally sera samples via superficial tail vein sampling were taken from the mice prior to the first immunisation dose and 14 days after the second dose.

The mouse sera samples obtained were assayed for some of the Streptococcus pneumoniae antibodies, IgG (7 Serotypes:—4, 6B, 9V, 14, 18C (detects 33F responses), 19F and 23F), by multi-analyte fluorescent detection (Luminex). This work was performed at the National Institute for Biological Standards and Control (NIBSC). For the other serotypes no kit was available and so the responses were not measured.

The Luminex multi-analyte fluorescent detection is based on microscopic beads (microspheres) internally labelled with two different fluorophores. When excited by a 635 nm laser, the fluorophores emit at different wavelengths, 658 nm and 712 nm. By varying the 658/712 emission ratios, an array of up to 100 different fluorescent profiles, called classifications, can be created. Using precision fluidics, digital signal processors, and advanced optics, the Luminex 100 analyser assigns each microsphere according to its predefined classification. Thus, multiple-bead classifications can be combined in a single sample. In the assay employed each individual pneumococcal polysaccharide serotype is covalently attached to a microsphere with a unique classification. During the assay procedure, all the different pneumococcal polysaccharide serotype microspheres are combined with a single dilution of test murine sample. Antibodies in the murine sample attach to pneumococcal polysaccharide antigens on the microspheres. The amount of antibody bound to the microspheres is determined with anti-mouse IgG conjugated to phycoerythrin. When excited at 532 nm, phycoerythrin emits at 575 nm. The fluorescence intensity at 575 nm is directly proportional to the amount of antibody bound to the microspheres. Since the analyte specificity and position of each bead classification in the array is known, a single fluorescent reporter molecule can be used to calculate specific antibody levels to all serotypes tested (represented by the polysaccharide-bead conjugates).
Results:—

FIG. 3 shows the calculated streptococcus pneumoniae antibodies, murine IgG (Serotypes specific responses:—4, 6B, 9V, 14, 18C (*see FIG. 3, detects 33F responses), 19F and 23F), by multi-analyte fluorescent detection. Bars represent the average response of the 5 mice dosed and the error bars are standard deviations, the empty bars are pre immunisation background response of the mice whilst the solid bar is the response following the immunisation schedule.
Comments The average response to all the seven serotypes tested were raised following immunisation with the blend (multivalent) of monoserotype liposomal compositions comprising of coentrapped pneumococcal polysaccharide and protein diphtheria toxin (197) CRM mutant within liposomes. The increase in response, post immunisation, relative to the pre immunisation response, was 1.8, 6.3, 1.4, 1.5, 2.5, 5.3 and 3.6 fold for the serotypes 4, 6B, 9V, 14, 33F, 19F and 23F fold respectively.

Thus the composition described demonstrates the ability to raise an antibody response to multivalent pneumococcal polysaccharide antigens in mice following immunisation with a blend (multivalent) of monoserotype liposomal compositions comprising coentrapped pneumococcal polysaccharide and protein diphtheria toxin (197) CRM mutant within liposomes.

EXAMPLE 3

Demonstration of Protective Efficacy to live Streptococcus pneumoniae (challenge) in mice, following immunisation of a blend (multivalent) of monoserotype liposomal compositions comprising coentrapped pneumococcal polysaccharide and protein Diphtheria Toxin (197) CRM Mutant within the liposomes with a pneumococcal polysaccharide vaccine (PNEUMOVAX®) boost.
Experimental Details:—

The following liposome formulations (ID21-34) were prepared, Table 3, using a conventional lipid film dry/hydration to MLV/sonication to SUV/DRV process (as in Example 1). Sucrose x3 lipid mass (SUV) was added to the SUV and material(s) to be entrapped at the SUV stage prior to DRV process to reduce the size of the resultant liposomes formed post the DRV stage.

Each formulation (ID21-34), consisted of an individual pneumococcal polysaccharide serotype coentrapped with a protein Diphtheria Toxin CRM197 mutant within liposomes.

TABLE 3

Liposomal mono PS entrapped formulations prepared. (ID21-34)

| Formulation ID | Lipid (SUV), mg | Diphtheria Toxin CRM197, μg | Pneumococcal Polysaccharide | |
|---|---|---|---|---|
| | | | μg | (Serotype) |
| ID21 | 16.6 | 158.4 | 66 | 1 |
| ID22 | 16.6 | 158.4 | 66 | 2 |
| ID23 | 16.6 | 158.4 | 66 | 4 |
| ID24 | 16.6 | 158.4 | 66 | 5 |
| ID25 | 16.6 | 158.4 | 66 | 6B |
| ID26 | 16.6 | 158.4 | 66 | 7F |
| ID27 | 16.6 | 158.4 | 66 | 9N |
| ID28 | 16.6 | 158.4 | 66 | 9V |
| ID29 | 16.6 | 158.4 | 66 | 12F |
| ID30 | 16.6 | 158.4 | 66 | 14 |
| ID31 | 16.6 | 158.4 | 66 | 15B |
| ID32 | 16.6 | 158.4 | 66 | 19F |
| ID33 | 16.6 | 158.4 | 66 | 23F |
| ID34 | 16.6 | 158.4 | 66 | 33F |

Material Details:

The lipidic materials used were Egg PC (E PC, 98% purity, Lipoid) and Cholesterol (Sigma). Pneumococcal capsular polysaccharide (Pn PS) equivalent to the American Type Culture Collection (ATCC) materials and Diphtheria Toxin CRM197 protein were obtained from the Serum Institute of India Limited (SIIL).

The liposomal mono PS entrapped formulations (ID21-34) were individually rehydrated (DRV process) and pooled together to make a multivalent formulation immediately for immunisation, via subcutaneous injection, of ten Balb/C mice (female). The dose of multivalent vaccine contained the equivalent of 14 monovalent formulations containing 0.2 μg Pneumococcal Polysaccharide and 0.48 μg Diphtheria Toxin CRM197 protein and 0.138 mg of lipid. Consequently, the multivalent (14 serotypes) vaccine administered to the mice contain in total 2.8 μg Pneumococcal Polysaccharide and 6.72 μg Diphtheria Toxin CRM197 protein and 1.935 mg of lipid.

Two groups of mice were immunised:—

Group 1 were immunised, 14 day interval between doses, with 3 doses of the blend (multivalent) of monoserotype liposomal compositions, followed by pneumococcal polysaccharide vaccine (PNEUMOVAX®) boost administered 8 weeks after the last liposomal formulation dose.

The PNEUMOVAX® dose administered consists of a mixture of highly purified capsular polysaccharides from 23 pneumococcal types of *Streptococcus pneumoniae*, serotypes (1 2 3 4 5 6B 7F 8 9N 9V 10A 11A 12F 14 15B 17F 18C 19F 19A 20 22F 23 F & 33F). The dose level administered for each purified capsular polysaccharides serotype was 7.5 μg and consequently the total polysaccharide dose administered was PNEUMOVAX® was 172.5 μg.

Group 2 were immunised, 14 day interval between doses, with 3 doses of pneumococcal polysaccharide vaccine (PNEUMOVAX®), followed by pneumococcal polysaccharide vaccine (PNEUMOVAX®) boost administered 8 weeks after the third PNEUMOVAX® dose.

Live *Streptococcus pneumoniae* challenge, was performed on all mice four weeks following the last dose. Briefly, mice were challenged intraperitoneally with 0.5 ml *S. pneumoniae* (serotype 6B) suspension prepared from fresh overnight colonies from a 5% horse blood agar plate were suspended in beef broth and further diluted to $4.0 \times 10^7$ CFU/ml.

The mice were observed for 6 days following administration of the bacterial challenge, and scored 0-4 based on their behaviour and clinical signs as below.

Score 0: healthy

Score 1: minor clinical signs of infection and inflammation e.g. observations of minor sign of distress and pain, changed activity, and social withdrawal.

Score 2: sever signs of infection like stiff movements, lack of curiosity, forced ventilation, changed body position, pilo-erection in the skin, or changes in movement.

Score 3: sever pain and the mouse was sacrificed immediately to minimise the suffering of the animal.

Score 4: the mouse was dead.

Results:—

The results are shown in Tables 4 and 5, of observed responses in mice following live *Streptococcus pneumoniae* challenge.

TABLE 4

Group 1

| mouse no. | Day 0 pm | Day 1 am | Day 1 pm | Day 2 am | Day 2 pm | Day 3 am | Day 4 am | Day 5 am | Day 6 am | Survival |
|---|---|---|---|---|---|---|---|---|---|---|
| 1 | 1 | 1 | 2 | 1 | 1 | 1 | 1 | 0 | 0 | 56% |
| 2 | 1 | 1 | 1 | 0 | 0 | 0 | 0 | 0 | 0 | |
| 3 | 1 | 4 | | | | | | | | |
| 4 | 1 | 4 | | | | | | | | |
| 5 | 1 | 4 | | | | | | | | |
| 6 | 0 | 1 | 2 | 1 | 1 | 2 | 1 | 1 | 1 | |
| 7 | | | | Died before challenge | | | | | | |
| 8 | 0 | 1 | 2 | 0 | 0 | 0 | 0 | 0 | 0 | |
| 9 | 0 | 0 | 0 | 0 | 0 | 0 | 0 | 0 | 0 | |
| 10 | 0 | 2 | 3 | | | | | | | |

TABLE 5

Group 2

| mouse no. | Day 0 pm | Day 1 am | Day 1 pm | Day 2 am | Day 2 pm | Day 3 am | Day 4 am | Day 5 am | Day 6 am | Survival |
|---|---|---|---|---|---|---|---|---|---|---|
| 1 | 0 | 0 | 0 | 1 | 2 | 3 | | | | 11% |
| 2 | 0 | 0 | 0 | 0 | 0 | 1 | 1 | 1 | 1 | |
| 3 | | 1 | 3 | | | | | | | |

TABLE 5-continued

| | Group 2 | | | | | | | | | |
|---|---|---|---|---|---|---|---|---|---|---|
| | Day 0 | Day 1 | | Day 2 | | Day 3 | Day 4 | Day 5 | Day 6 | |
| mouse no. | pm | am | pm | am | pm | am | am | am | am | Survival |
| 4 | | 0 | 3 | | | | | | | |
| 5 | | | | Died before challenge | | | | | | |
| 6 | | 2 | 3 | | | | | | | |
| 7 | | 2 | 4 | | | | | | | |
| 8 | | 1 | 1 | 1 | 4 | | | | | |
| 9 | | 2 | 4 | | | | | | | |
| 10 | | 2 | 4 | | | | | | | |

Comments:

The results demonstrate that mice are better protected against live *Streptococcus pneumoniae* challenge (serotype 6B), following immunisation of a blend (multivalent) of monoserotype liposomal compositions comprising of coentrapped pneumococcal polysaccharide and protein Diphtheria Toxin (197) CRM Mutant within liposomes with a pneumococcal polysaccharide vaccine (PNEUMOVAX®) boost compared to immunisation with pneumococcal polysaccharide vaccine (PNEUMOVAX®) alone.

The invention claimed is:

1. A liposomal composition comprising coentrapped within liposomes a polysaccharide antigen and a protein carrier;
   wherein the polysaccharide antigen is water-soluble;
   the protein carrier has at least one T-cell epitope, a molecular weight of at least 35 kDa, is non-toxic and is tetanus toxoid or diphtheria toxoid;
   wherein the polysaccharide antigen and protein carrier are non-conjugated; and
   wherein the liposomes have an average diameter in the range 50-700 nm and are formed from liposome forming compounds that have, in combination, no overall ionic charge and comprise at least one phospholipid.

2. The composition of claim 1, wherein the liposome forming compounds comprise cholesterol.

3. The composition of claim 1, wherein the liposome forming compounds include at least one cationically charged compound.

4. The composition of claim 1, wherein the at least one phospholipid includes phosphatidylcholine, optionally in combination with phosphatidylethanolamine.

5. The composition of claim 1, wherein the liposomes have an average diameter in the range 80-500 nm.

6. The composition of claim 1, wherein the ratio of polysaccharide antigen to protein carrier is in the range 6:1 to 1:6.

7. The composition of claim 6, wherein the ratio of polysaccharide antigen to protein carrier is in the range 4:1 to 1:3.

8. The composition of claim 1 in unit dosage form.

9. The composition of claim 8, wherein each unit dosage comprises 1-30 µg protein carrier.

10. The composition of claim 1, wherein the polysaccharide antigen has no overall ionic charge.

11. The composition of claim 1, wherein the polysaccharide antigen is a T-cell independent antigen.

12. The composition of claim 11, wherein the polysaccharide antigen is derived from an infectious agent.

13. The composition of claim 11, which comprises more than one polysaccharide antigen.

14. The composition of claim 13, wherein the antigens are derived from the same bacterial species.

15. The composition of claim 13, wherein each antigen is encapsulated in a separate population of liposomes.

16. The composition of claim 13, wherein several antigens are co-encapsulated in the same liposomes of the population.

17. The composition of claim 1, which is aqueous and in which the liposomes are suspended in a continuous aqueous medium.

18. The composition of claim 1, which is in dry form.

19. The composition of claim 1, additionally comprising one or more sugars.

20. The composition of claim 1, which is a pharmaceutical composition and comprises a pharmaceutically acceptable diluent or excipient.

21. The composition of claim 1, wherein the polysaccharide antigen is entrapped in the intravesicular space of the liposomes.

22. The composition of claim 1, wherein the protein carrier is entrapped in the intravesicular space.

23. A method to elicit an immune response to a polysaccharide antigen in a mammal which method comprises administering to a mammal in need of such response an effective amount of the composition of claim 1.

24. The method of claim 23, wherein the immune response comprises production of IgG, IgM or IgA specific to the polysaccharide antigen.

25. The method of claim 23, wherein the said administering is subcutaneously, intravenously, intraperitoneally, intramuscularly, intranasally, by inhalation, intravaginally, buccally or orally.

26. The method of claim 25, wherein the administering is sub-cutaneously.

27. The method of claim 23, wherein the composition is administered in a unit dosage comprising 1-30 µg protein carrier.

28. The method of claim 23, wherein the immune response is protective against infection by the microbe from which the polysaccharide antigen is derived.

29. The method of claim 23, wherein the mammal is a human.

30. A method for forming a liposomal composition of claim 1, comprising
   (I) mixing empty liposomes with a polysaccharide antigen and protein carrier; and
   (ii) drying the mixture from step (I) wherein the polysaccharide antigen is water-soluble;
   the protein carrier has at least one T-cell epitope, a molecular weight of at least 35 kDa, is non-toxic and is tetanus toxoid or diphtheria toxoid;
   wherein the polysaccharide antigen and protein carrier are non-conjugated; and wherein the liposomes have an average diameter in the range 50-700 nm and are formed from liposome forming compounds that have, in combination, no overall ionic charge and comprise at least one phospholipid.

31. The method of claim 30, which further comprises the step of rehydrating the mixture from step (ii) to form a suspense of dehydration-rehydration vesicles (DRV).

32. The method of claim 31, in which non-entrapped material is at least partially removed from the DRVs.

33. The method of claim 30, wherein in step (I), a sugar is present in the mixture of empty liposomes, protein and polysaccharide antigen.

\* \* \* \* \*